United States Patent [19]

Kumar et al.

[11] Patent Number: 4,748,263

[45] Date of Patent: May 31, 1988

[54] AROMATIC CYCLOTRIPHOSPHAZENES

[75] Inventors: Devendra Kumar, Shakarpur Extension, India; George M. Fohlen, Millbrae; John A. Parker, Los Altos, both of Calif.

[73] Assignee: The United States of America as represented by the administrator of the National Aeronautics and Space Administration, Washington, D.C.

[21] Appl. No.: 924,467

[22] Filed: Oct. 29, 1986

Related U.S. Application Data

[62] Division of Ser. No. 760,374, Jul. 30, 1985, Pat. No. 4,634,759, which is a division of Ser. No. 599,126, Apr. 11, 1984, Pat. No. 4,550,177.

[51] Int. Cl.$^4$ ................................................ C07F 9/00
[52] U.S. Cl. .......................................... 558/80; 564/13
[58] Field of Search .............................. 558/80; 564/13

[56] References Cited

U.S. PATENT DOCUMENTS 3,280,222 10/1966 Kober et al. .......................... 558/80

FOREIGN PATENT DOCUMENTS 320498 11/1971 U.S.S.R. ................................. 558/80

Primary Examiner—Anton H. Sutto

[57] ABSTRACT

4-Aminophenoxy cyclotriphosphazenes are reacted with maleic anhydride to produce maleamic acids which are converted to the maleimides. The maleimides are polymerized. By selection of starting materials (e.g. hexakis amino or trisaminophenoxy-trisphenoxy-cyclotriphosphazenes), selection of molar proportions of reactants, use of mixtures of anhydrides and use of dianhydrides as bridging groups a variety of maleimides and polymers are produced. The polymers have high limiting oxygen indices, high char yields and other useful heat and fire resistant properties making them useful as, for example, impregnants of fabrics.

3 Claims, 9 Drawing Sheets

SCHEME I

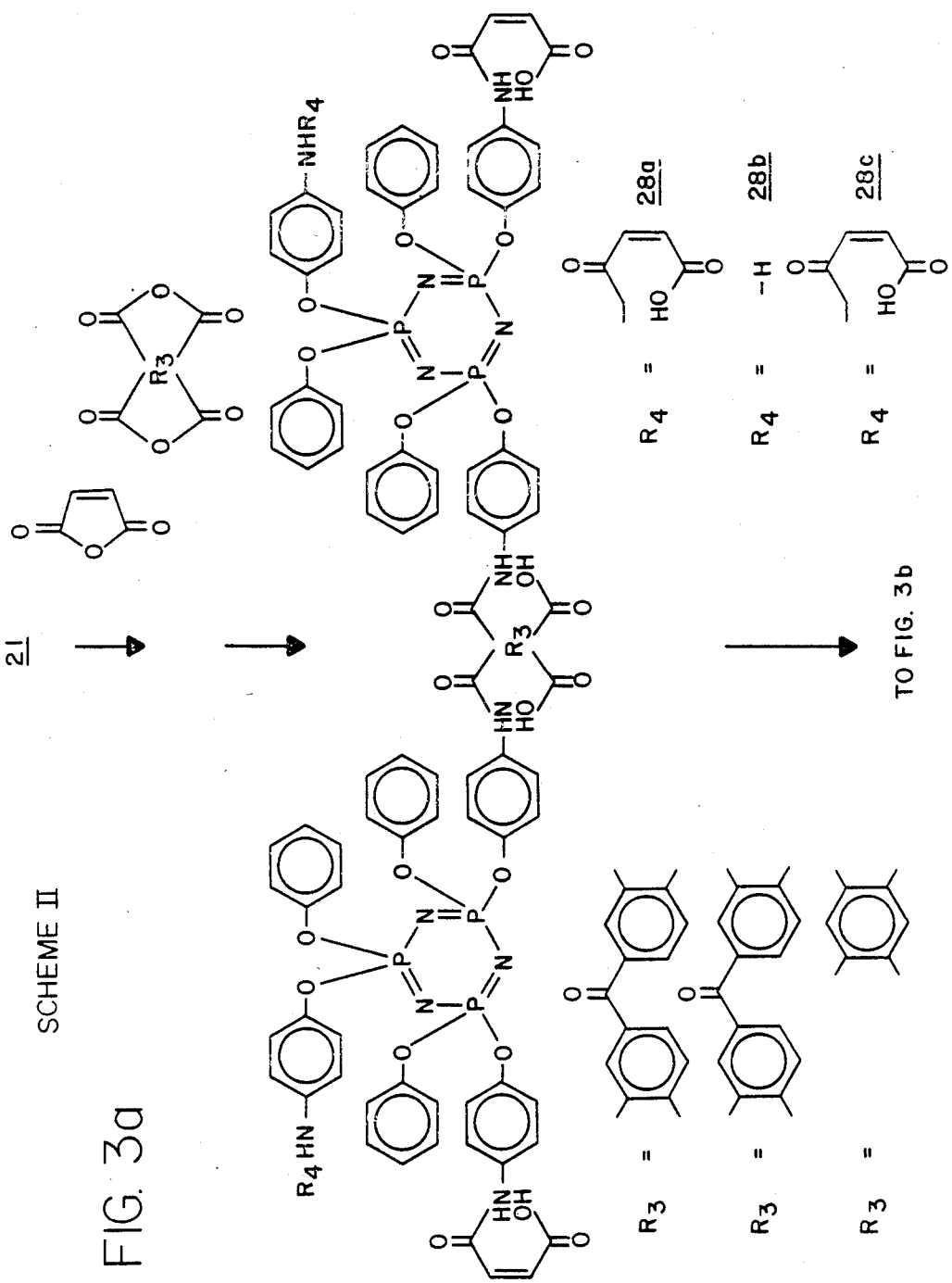
FIG. 3a SCHEME II

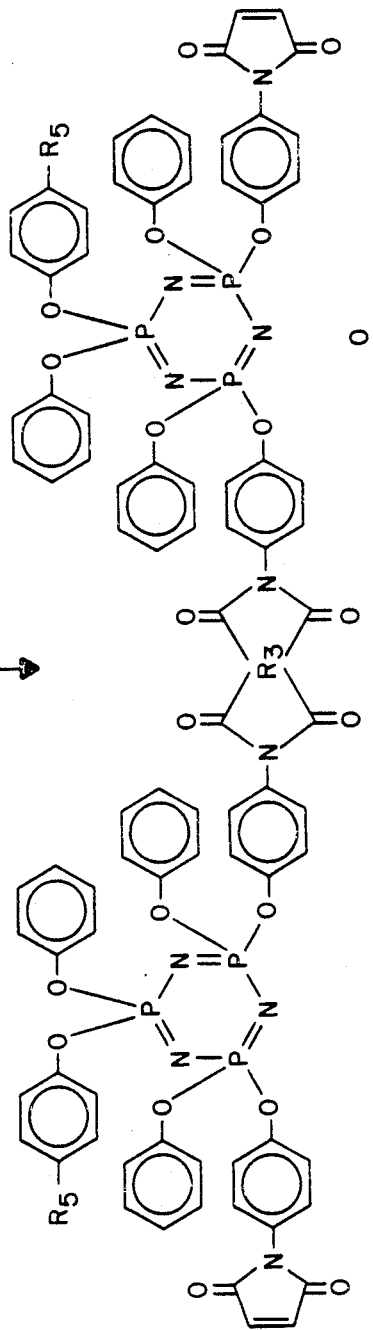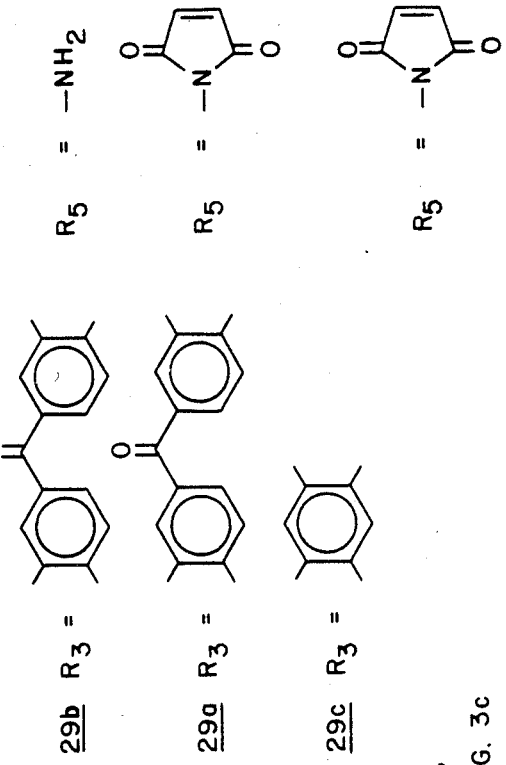
FIG. 3b SCHEME II (continued)

SCHEME II (concluded)

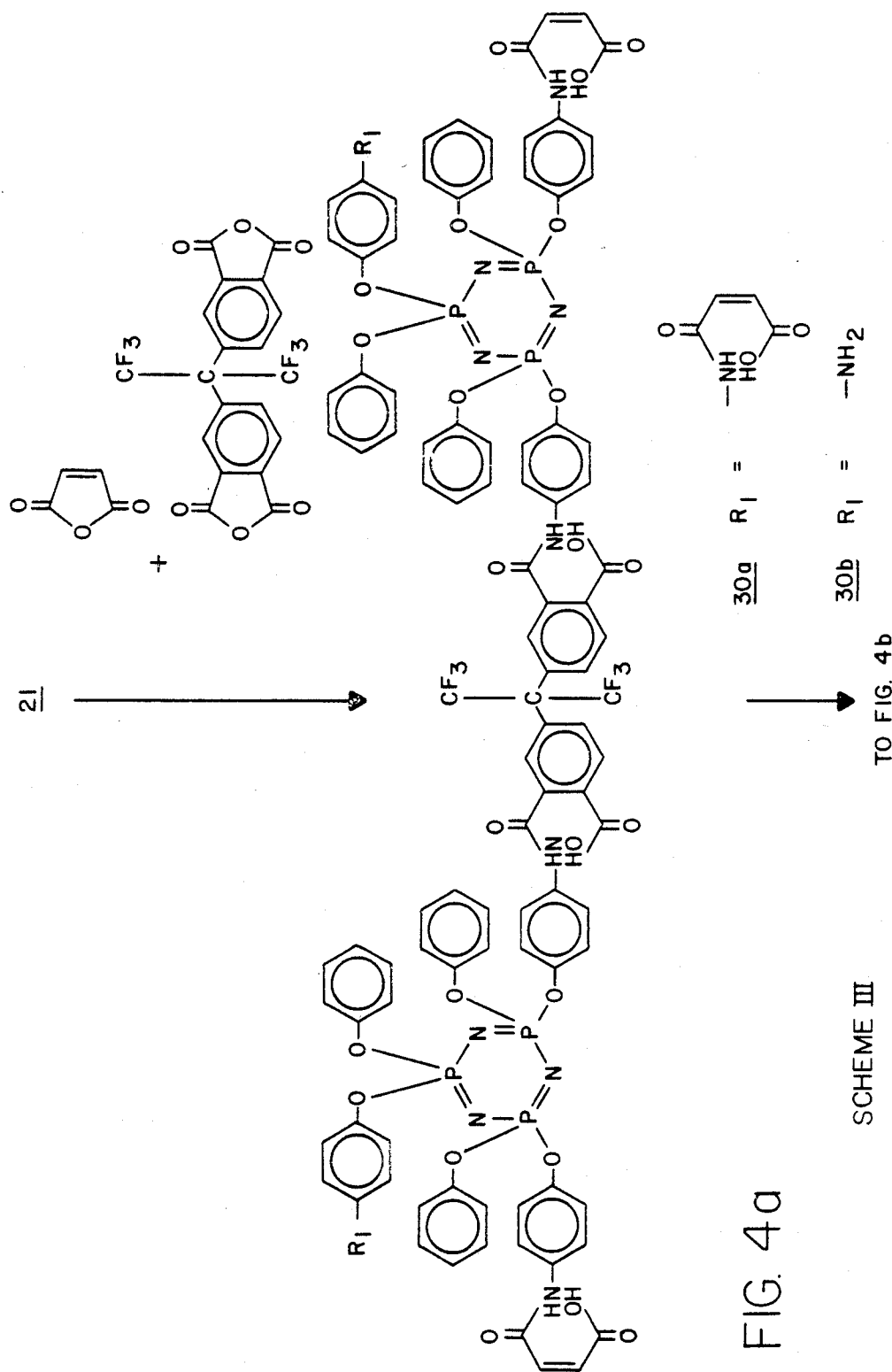
FIG. 4a SCHEME III

SCHEME III (concluded)

AROMATIC CYCLOTRIPHOSPHAZENES

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

This application is a division of Ser. No. 760,374, filed July 30, 1985, now U.S. Pat. No. 4,634,759, which is a division of Ser. No. 599,126, filed Apr. 11, 1984, now U.S. Pat. No. 4,550,177.

FIELD OF THE INVENTION

The invention relates to fire and heat resistant polymers derived from hexachlorocyclotriphosphazene by replacement of the chlorine atoms with phenoxy or anilino groups some or all of which have amino groups, reacting the amino groups with an unsaturated anhydride such as maleic anhydride to produce a maleamic acid, converting the maleamic acid to a maleimide and polymerizing the maleimide. Such polymers are useful for laminating purposes.

BACKGROUND OF THE INVENTION

Certain phosphorus-containing organic compounds are known to be fire retardant and heat resistant when mixed with or incorporated chemically in polymers. However such mixtures degrade the polymers. Many instances of polymers are known in which phosphorus and nitrogen atoms are alternatively linked into a long linear polymer chain with various substituents appended onto the P atoms. These polymers are used in specialized heat resistant elastomers for example. These linear chains have been shown to degrade thermally to form the cyclic phosphazene ring indicating the greater stability of this latter structure. In accordance with the present invention phosphorus is incorporated in the polymer molecules in the form of the cyclic phosphazene ring.

OBJECTS OF THE INVENTION

It is an object of the invention to provide fire and heat resistant polymers which are improved with respect to one or more of the properties, such as limiting oxygen index (LOI), char yield in both nitrogen and air, and release of noxious gases.

DESCRIPTION OF THE DRAWINGS

FIG. 3a represents the case where one of the anhydrides employed with maleic anhydride is a dianhydride which provides a bridging group between two cyclotriphosphazene moieties, and it shows the production of maleamic acids;

FIG. 3b shows the conversion of the maleamic acids of FIG. 3a to maleimides;

FIG. 4a is similar to FIG. 3a but illustrates another bridging group; and

BRIEF SUMMARY OF THE INVENTION

Figure 1A:
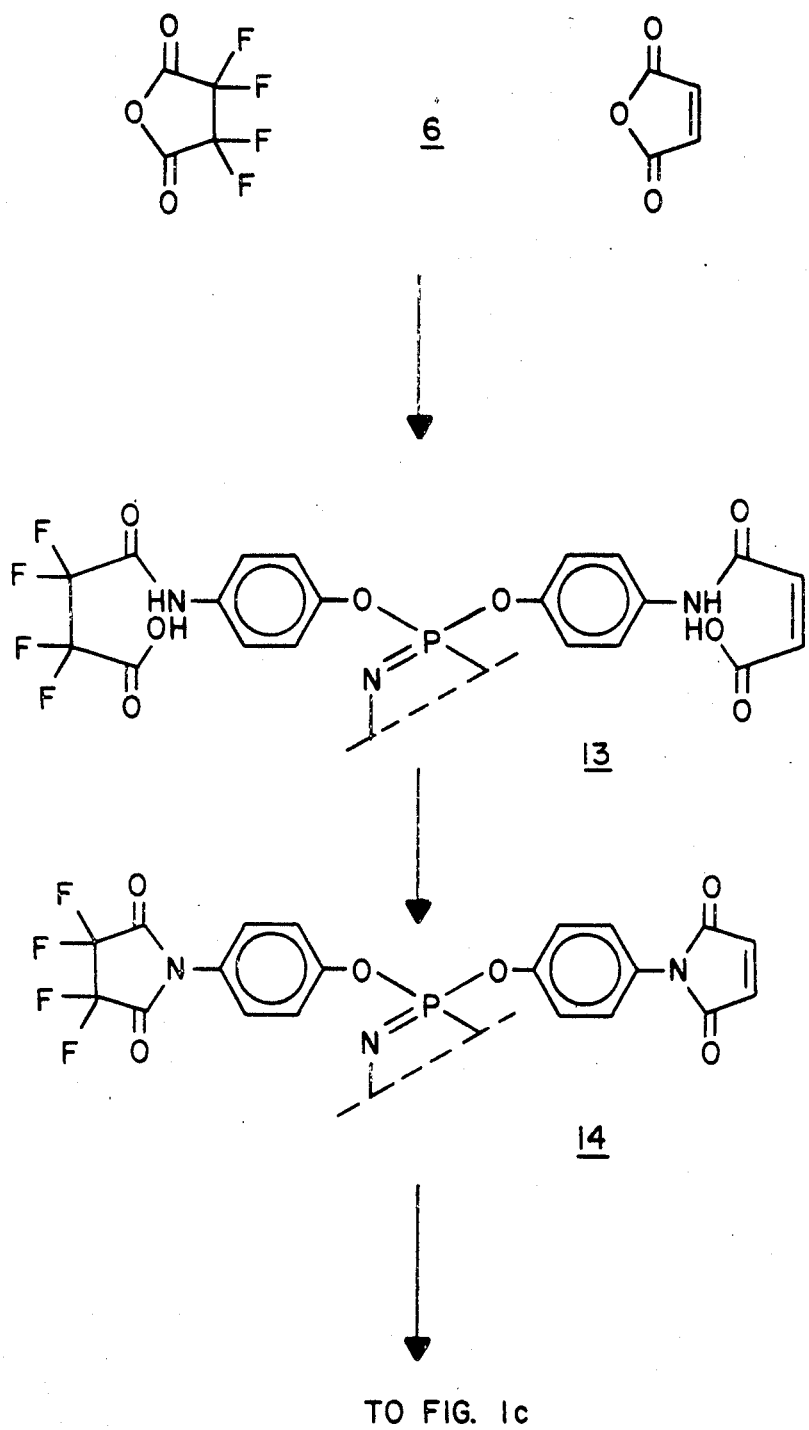
FIG. 1a represents the reaction of a mixture of maleic anhydride and tetrafluorosuccinic anhydride with hexakis(4-aminophenoxy)cyclotriphosphazene to produce a maleimide.

The invention relates to polymers based upon hexachlorocyclotriphosphazene 1

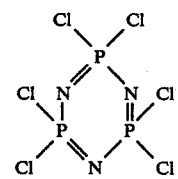

in which all of the chlorine atoms (which may be substituted by other replaceable atoms or groups of atoms, e.g. Br) are replaced by phenoxy or anilino groups to produce a polymer precursor 2

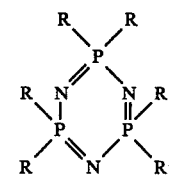

in which the groups R are phenoxy or anilino groups some or all of which are substituted by amino groups.

The amine compounds 2 are then reacted with an ethylenically unsaturated acid anhydride such as maleic anhydride to form a maleamic acid 4 which may be illustrated as follows [reaction (1)]:

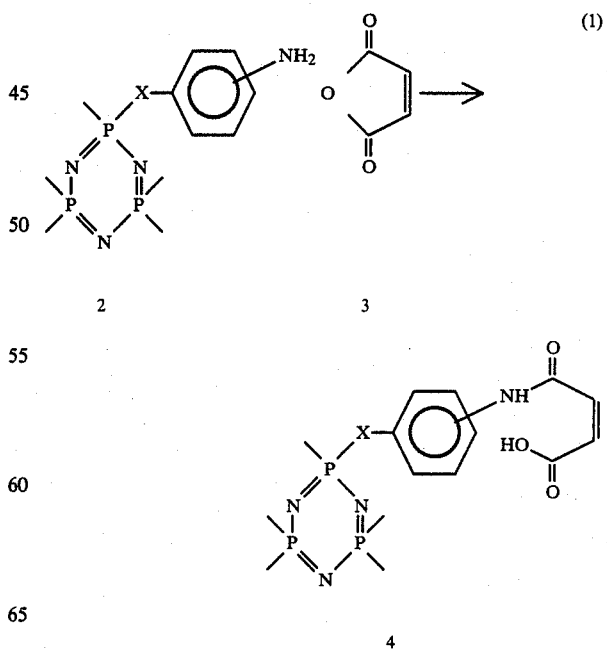

where X=O< or >NH.

The maleamic acid 4 is heated or chemically treated to cause ring closure and to produce the maleimide 5

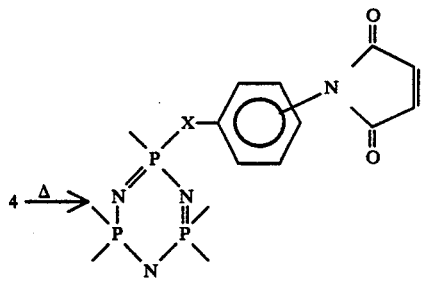

The maleimide 5 is then heated, in the presence of a catalyst if necessary, to cause polymerization. If there are free amino groups in 4 (i.e. insufficient maleic anhydride is used to react in reaction (1) with all of the amino group) one type of reaction will occur in which an amino group adds to the vinyl group derived from maleic anhydride. This is illustrated by Example 5. If all of the amino groups are reacted in reaction (1) with maleic anhydride, the polymer will be the product of vinyl type polymerization. This is illustrated in Example 6.

As will become apparent from the detailed description of the invention other vinyl type dicarboxylic acid anhydrides may replace maleic anhydride, a mixture of anhydrides may be used in reaction (1) and many other variants may be employed.

Examples 1 and 2 below illustrate the preparation of phenoxy and anilino substituted cyclotriphosphazenes containing amino groups by first forming the nitro compounds and reducing the nitro groups to amino groups. A preferred method which avoids the intermediate nitro compounds is described below.

The resins of this invention may be used with fillers or fibrous materials to form heat and fire resistant composites. Suitable fibrous additives are fibers of graphite, glass, silicon carbide, aramid and polyflorocarbon.

DETAILED DESCRIPTION OF THE INVENTION

EXAMPLE 1

Preparation of Hexakis(4-nitrophenoxy)cyclotriphosphazene A

The formula is as follows

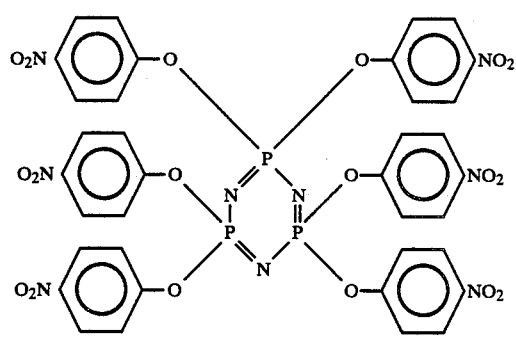

Hereafter such formulas in which the cyclotriphosphazene ring is substituted on the three phosphorus atoms by the same groups will be abbreviated. General abbreviated formulas such as

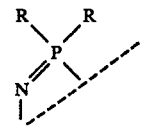

are used where the R's may be the same or different and it is understood that there are two other such groupings

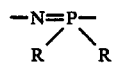

on the cyclotriphosphazene ring.

To a 500 ml four-necked flask equipped with a stirrer, nitrogen inlet, thermometer and a Dean-Stark water separator, xylene (120 ml) and a powdered mixture of 4-nitrophenol (35.82 g) and potassium hydroxide (16.11 g) was added while maintaining continuous vigorous stirring and a nitrogen atmosphere. The orange mixture was heated slowly to 80° C. At this temperature, hexachlorocyclotriphosphazene (12 g) in xylene (20 ml) was added dropwise over a period of 0.5 h. The mixture was heated to reflux until about 6 ml of water (3 h) had collected in the Dean-Stark distillation trap. The light yellow solid obtained was filtered and dried. This crude solid was stirred with 10% aqueous potassium hydroxide, filtered and washed with warm water. The white solid obtained was dried and recrystallized twice from o-dichlorobenzene to yield 25 g of A, m.p. 261°–264° C. The structure was identified in this example and in the examples below by procedures such as mass spectroscopy, infrared, $^1$H-NMR and chemical analysis.

EXAMPLE 2

Preparation of Hexakis(4-aminophenoxy)cyclotriphosphazene 6

The formula (abbreviated) is

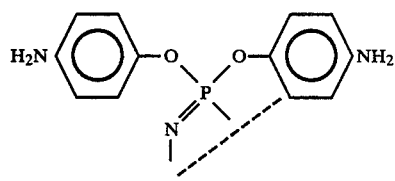

A 250 ml heater equipped autoclave pressure bottle was charged with a solution of A (10.0 g) in aniline (40 ml) containing catalyst, platinum oxide (0.05 g). The mixture was agitated vigorously at 50° C. and 60 psi of hydrogen until no further pressure drop was observed (8–10 h). The reaction mixture was filtered and concentrated to 20 ml under reduced pressure and poured slowly into benzene or toluene (200 ml). The gray solid obtained after maceration was crystallized from o-dichlorobenzene to yield 6 (6.0 g).

EXAMPLE 3

Preparation of the Trisamino-Trismaleamic Acid 7

The formula is and vinyl groups the polymer molecule will contain preponderantly the following structure

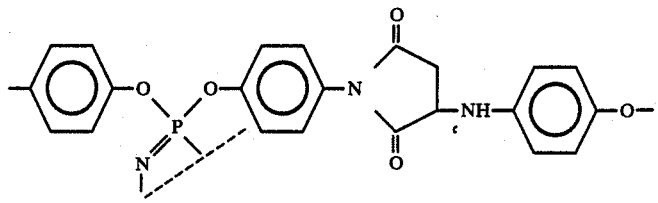

resulting from addition of amino groups to the vinyl group and possibly some

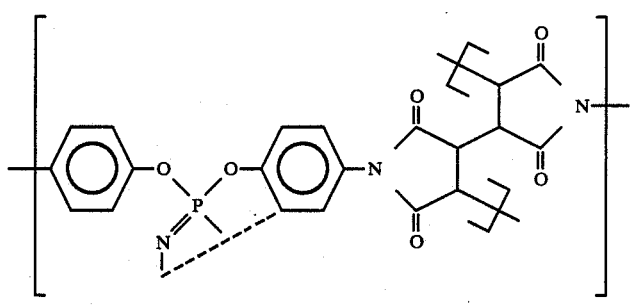

from the vinyl-vinyl addition reaction.

EXAMPLE 6

Preparation of Various Hexakis Maleamic Acids and of the Corresponding Maleimides and Polymerization of the Maleimides (a) Preparation of Hexakis(4-maleamic acid phenoxy)cyclotriphosphazene 11

The formula is

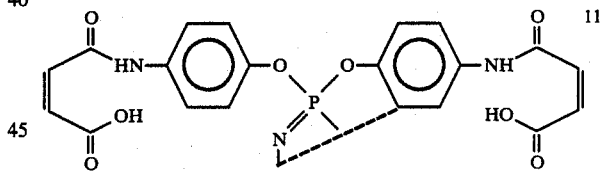

To a stirred solution of 6 (3.91 g, 0.005 mole) in acetone (100 ml), granular maleic anhydride (2.94 g, 0.03 mole) was added at ambient temperature in the presence of a nitrogen atmosphere. A light yellow solid separated soon after the addition and the mixture was stirred further for 2 h. The solid was filtered, washed with acetone and dried to yield the desired maleamic acid 11, m.p. 159°–160° C.

(b) Preparation of the Maleimide 12
The formula is

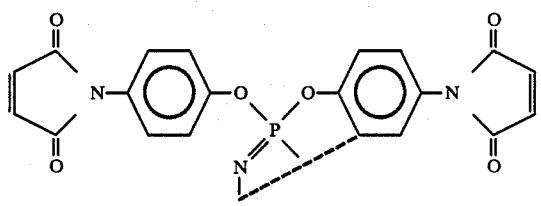

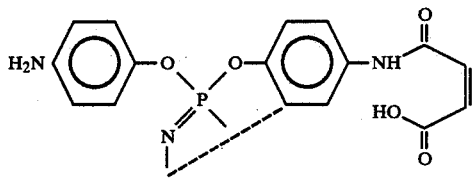

To a stirred solution of 6 (2.5 g, 0.0032 mole, in dry DMAC 12 ml), granular maleic anhydride (1.05 g, 0.0107 mole) was added in the presence of nitrogen atmosphere. The yellow solution obtained was stirred for 8–10 h and then poured over crushed ice. The light yellow solid obtained was filtered, washed with water and dried to yield the required amic acid 7 (3.2 g), m.p. 300° C.

EXAMPLE 4

Preparation of the Maleimide 8

The formula is

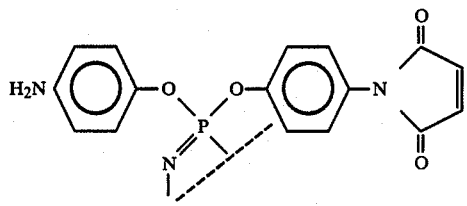

A solution of 7 in DMAC was heated with stirring in a nitrogen atmosphere at 160°–165° C. for 0.75–1.0 h to yield the corresponding maleimide 8 as a yellow solid.

EXAMPLE 5

Polymerization of the Maleimide 8

A 25% solution of 8 in DMAC was heated in an air oven at 160°–162° C. for 0.25 h and then at 232°–233° C. for 1.5 h, the brownish solid obtained was further heated to 285° for 0.5 h to give a tough dark brown polymer. Since the maleimide 8 has both amino groups A solution of 11 in DMAC was stirred under a nitrogen atmosphere and heated to 170°–180° C. for 2.5 h. The solution was cooled and poured over ice to give the desired hexamaleimide 12 as yellow solid.

(c) Polymerization of 12

Yellow powder of 12 or its solution in DMAC was polymerized using similar curing conditions as in Example 5.

The repeating unit is

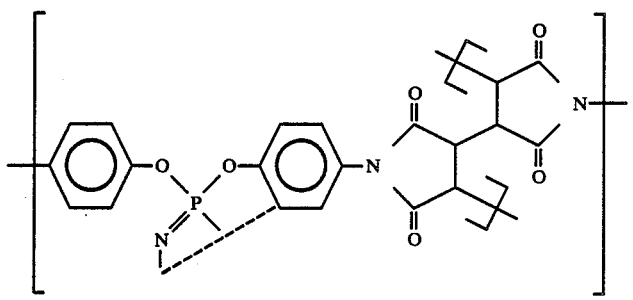

(d) Reaction of 6 with a Mixture of Maleic Anhydride and Perfluorosuccinic Anhydride, Conversion of the Maleamic Acid to Maleimide and Polymerization of the Imide The reaction scheme was as shown in FIG. 1 in which R is

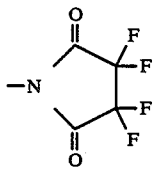

To a three-necked flask (10 ml) equipped with magnetic stirrer, nitrogen purge, condenser and drying tube, a solution of 6 (0.3 g, 0.00038 mole) in DMAC (5 ml) was added and continuously stirred. Perfluorosuccinic anhydride (0.137 ml, 0.00128 mole) was injected into the DMAC solution with a syringe and soon after, granular maleic anhydride (0.1261 g, 0.00128 mole) was added. The light-yellow solution was stirred for 0.5 h in a nitrogen atmosphere to give the desired maleamic acid 13.

The continuously stirred solution of maleamic acid 13 in presence of a nitrogen atmosphere was heated in an oil bath maintained at 150°–160° for 1.5 h and then at 170°–180° for 1.5 h. The reaction was allowed to cool and then poured over crushed ice. Light gray solid obtained on maceration was filtered, washed with water, and dried to give the maleimide 14, m.p. 152°–155° C.

Maleimide 14 was heated in air oven previously maintained at 160°–162°. It melts and resolidifies. Heating at this temperature was continued for 0.5 h. The curing temperature was raised to 225° C. for 2 h and 300° C. for 1 h to give brown polymer having the repeating mer unit 15.

Figure 1B:
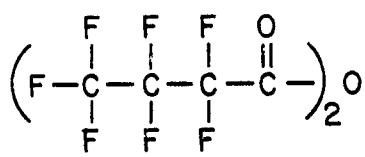
FIG. 1b represents a similar reaction in which perfluorobutyric anhydride is used instead of the tetrafluorosuccinic anhydride.
Figure 1B:
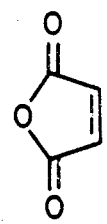
Figure 1B:
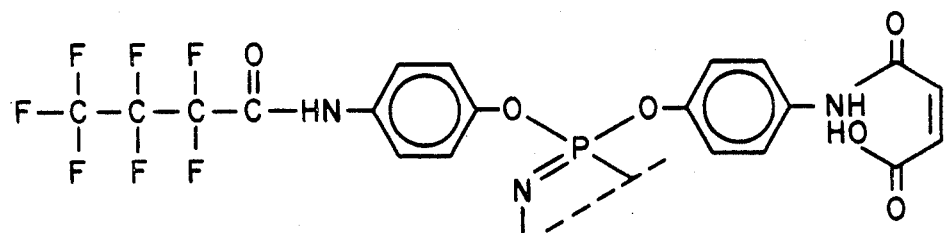
Figure 1B:
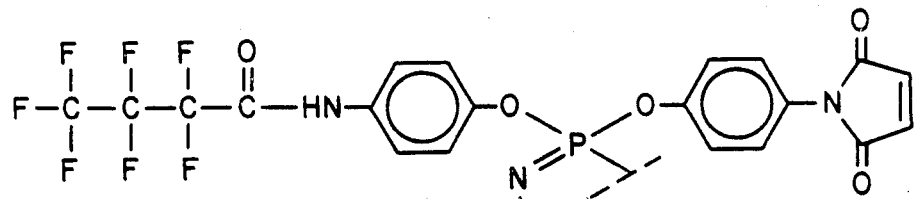
Figure 1C:
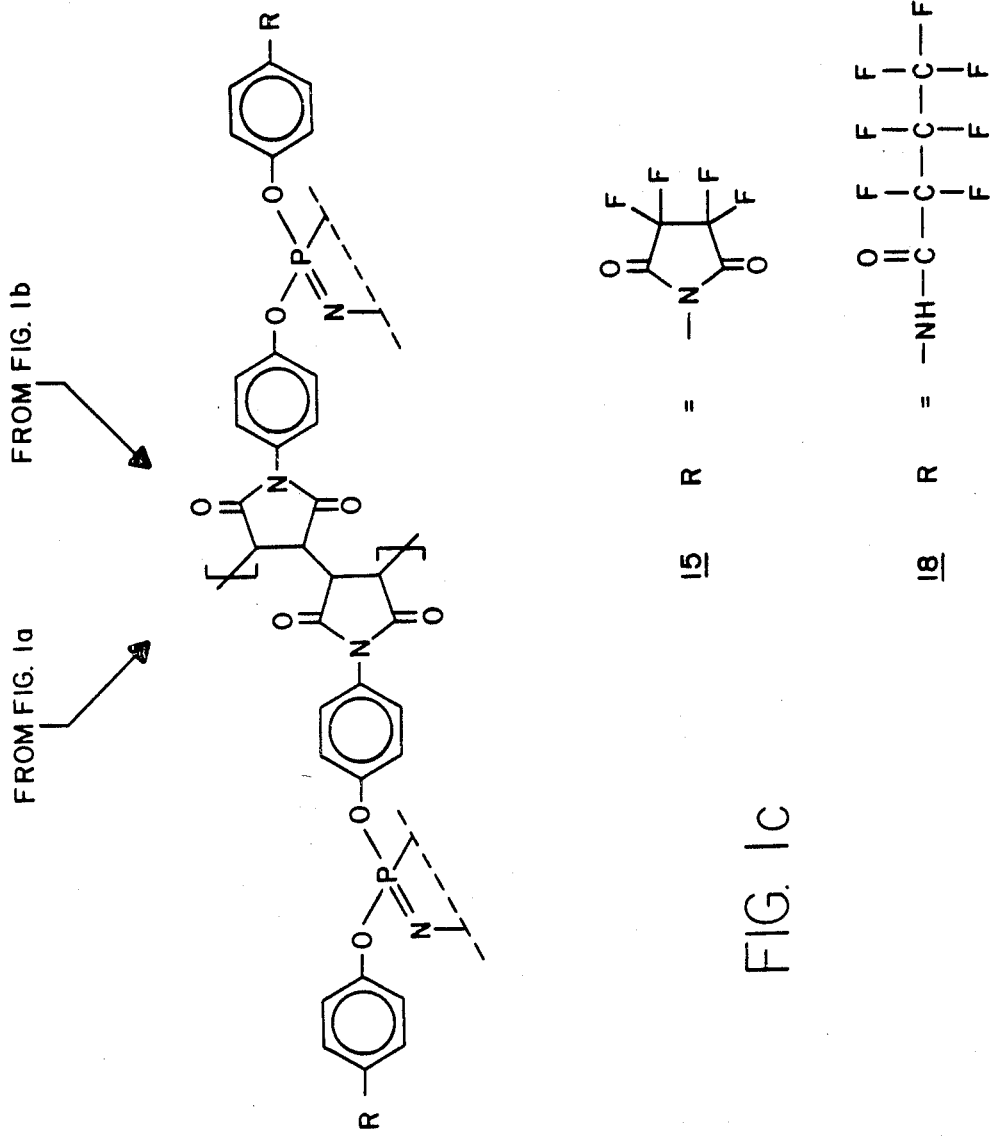
FIG. 1c represents the polymerization of the maleimides of FIGS. 1a and 1b.

(e) Reaction of 6 with a Mixture of Perfluoro Butyric Anhydride and Maleic Anhydride, Conversion of the Maleamic Acid to Maleimide and Polymerization of the Imide The reaction scheme was as shown in FIGS. 1a, 1b and 1c where R is

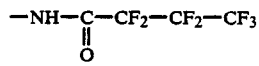

Following a method similar to Example 6(d), maleamic acid 16 was obtained by the reaction of perfluorobutyric anhydride (0.264 ml) and maleic anhydride (0.105 g) with 6.

The solution of maleamic acid 16 was heated at 160°–165° for 0.5 h to yield the required maleimide 17.

Thermal polymerization of maleimide 17 gave polymer 18 using similar conditions of curing.

The thermal stabilities of the polymers of Examples 5, 6(c) and 6(d) were investigated by dynamic thermogravimetric analyses in air or nitrogen atmospheres. The polymer decomposition temperatures (PDT), the temperatures at which the polymers' maximum rate of weight loss occurred ($PDT_{max}$), and the char yields, both in air and nitrogen, are summarized in Table I. The results show that the threshold temperature at which major fragmentation occurs for the polymers of Examples 5, 6(c) and 6(d) is 380°–400° C. both in air and nitrogen with maximum thermo-oxidative decomposition taking place mainly beyond 700° C. in all the polymers.

It is interesting to note that these polymers show higher char yields in nitrogen and particularly in air than most of the bismaleimides and other known polymers which are presently in use for complete fabrication. The polymer of Example 5 showed char yields of 82% at 800° C. in nitrogen and 81% at 700° C. in air. Similar higher char was obtained from polymers of Examples 6(c) and 6(d). The polymers of Examples 5 and 6(c) did not burn or melt when exposed to flame indicating their virtually incombustible nature. From these results it is apparent that the polymer of Example 5 is superior in fire- and heat-resistance to known phosphorus-containing polymers presently in use.

The observation of higher char yields may be explained due to the presence of unique combination and percentages of phosphorus, nitrogen and carbonyls in these polymers such that the thermo-oxidative decomposition is reduced. Minor weight loss observed in air for the polymer of Example 6(d) near 530° C. may be due to the presence of fluorine in the chain. These polymers on heating to 800° C. showed metallic type of luster.

Isothermal TGAs of the polymer of Example 5 were performed both in air and nitrogen atmospheres at 260° C., 350° C., 450° C., 550° C. and 700° C., respectively. In nitrogen on heating at 350° C. for 24 h, no weight loss was observed. In air, after 72 h at 260° C., about 4% weight loss occurred and at 350° C., the weight loss was about 35%. In air the rate of decomposition is rapid during first four hours of heating and then slows down.

EXAMPLE 7

Composite Fabrication

Test laminates were prepared by coating graphite cloth (eight-harness satin weave cloth, designed as style 133 fabric), with a dimethylacetamide solution of cyclotriphosphazene-maleimide 8 and drying the prepregs in an air oven at 105°–110° C. for 10 min. The prepregs (four or nine plies) were stacked in a vacuum-bag and pressed between aluminum plates in a heated press maintained at 160°–162° C. for 20 min, 232° C. for 1.5 h, and 290° for 0.5 h. The pressure during curing was maintained at about 50–70 psi.

The resin contents of the laminates were determined by boiling with hydrazine hydrate. The limiting oxyen index tests (LOI) were performed both at room temperature and at 300° C. (Table II). The laminates did not burn in pure oxygen even when heated to 300° C. prior to attempting to ignite them by flame indicating the outstanding flame resistance of the polymer of Example 5.

Dynamic mechanical analysis (DMA) determinations were performed on four-ply laminates obtained from 8. The glass transition temperature (Tg) of the cured sample was found to be 385° C.

The density, shear, tensile and flexural strength of a 9-ply laminate were determined and the values are shown in Table II.

TABLE I

Decomposition Temperatures and Char Yields of Polymers of Ex. 5 and 6

| | In $N_2$ | | | In Air | | | |
|---|---|---|---|---|---|---|---|
| Polymer | PDT (°C.) | $PDT_{max}$ (°C.) (W*) | Char Yield % 800° C. | PDT (°C.) | $PDT_{max}$ (°C.) (W*) | Char Yield % at 700° C., | 800° C. |
| Ex. 5 | 380 | — | 82 | 380 | 770 (73) | 81 | 65 |
| Ex. 6(c) | 395 | 420 (93) | 76 | 395 | 420 (93) 770 (59) | 75 | 50 |
| Ex. 6(d) | 380 | 395 (90) | 65 | 380 | 530 (70) 760 (50) | 60 | 42 |

(W*) = residue at indicated temperature.

TABLE II

Physical Properties of Graphite Cloth Laminates Based on Polymer of Example 5

| PROPERTY TESTED | TEST METHOD | VALUE |
|---|---|---|
| Resin Content | Hydrazine method | 22% |
| Density, g/cm³ | | 1.47 |
| LOI (room temperature) | ASTM D 2863 | 100% |
| (300° C.) | | 100% |
| Tensile Strength | ASTM D 638 | 58,014 psi |
| | | 400 $MN/m^2$ |
| Elongation at break | | 2.65% |
| Tensile Modulus | ASTM D 638 | 4.7 × $10^6$ psi |
| | | 32,407 $MN/m^2$ |
| Flexural Strength | ASTM D 790 | 50,347 psi |
| | | 347 $MN/m^2$ |
| Flexural Modulus | ASTM D 790 | 7,33 × $10^6$ psi |
| | | 50,547 $MN/m^2$ |
| Short Beam Shear | ASTM D 2344 | 4247 psi |
| | | 29.3 $MN/m^2$ |

Figure 2:
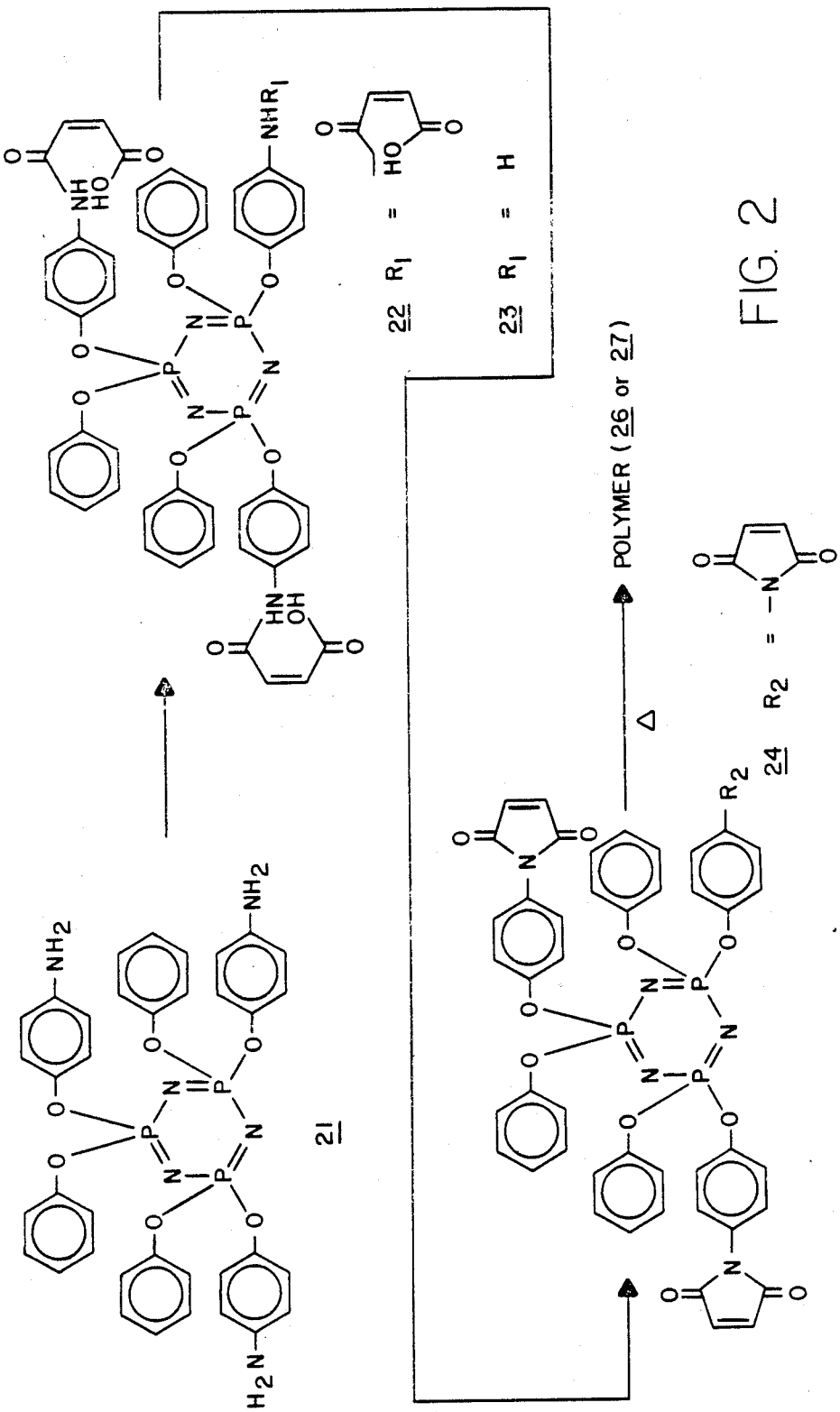
FIG. 2 represents the case where a trisphenoxytris 4-aminophenoxy compound is reacted with maleic anhydride.

Examples 8 to 12 below illustrate embodiments of the invention in which hexachlorocyclotriphosphazene (compound 1) is reacted first with sodium phenoxide to produce an intermediate (trischlorotrisphenoxycyclotriphosphazene), 19 which is then reacted without separation with sodium 4-nitrophenoxide to afford tris(4-nitrophenoxy)tris(phenoxy)cyclotriphosphazene 20. The nitro groups of 20 are reduced to afford the corresponding tris amino compound 21 which is then used according to Scheme I or Scheme II shown in FIG. 2 and FIG. 3, respectively.

Scheme I. Compound 21 is reacted with two or three mol-equivalents of maleic anhydride to afford a bis- or tris-maleamic acid 22 or 23 which is caused to undergo ring closure to afford the corresponding imide 24 or 25. The imide is polymerized to produce polymer 26 or polymer 27, respectively.

Scheme II. Compound 21 is reacted with maleic anhydride and with a dianhydride which serves to link two cyclotriphosphazene moieties. Maleamic acids result which are converted to maleimides which are polymerized.

In Scheme I (FIG. 2) $R_1$=H or

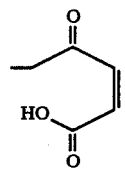

according to whether two or three mols of maleic anhydride are reacted with one mol of the tris amino compound 21.

In Scheme II (FIG. 3) $R_4$ likewise is H or

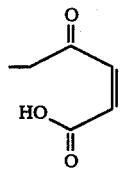

according to whether the tris amino compound has reacted with two or three mols of maleic anhydride. Also, in Scheme II in the linking or bridging group, $R_3$ is the group indicated depending upon the dianhydride.

EXAMPLE 8

Preparation of Compound 20

In a 500-ml, three-necked flask equipped with a nitrogen inlet, a calcium chloride guard tube, and a condenser, a solution of 1 (13.904 g, 0.04 mole) in 80 ml of THF was magnetically stirred. To this, a solution of sodium phenoxide prepared from phenol (11.293 g, 0.12 mole) and sodium hydride (5.25 g) in THF (50 ml) was added dropwise at ambient temperature. The stirred mixture was allowed to reflux in an oil bath; there was a continuous purge of nitrogen. After 48 h, a slurry of sodium 4-nitrophenoxide, prepared from 4-nitrophenol (16.693 g, 0.12 mole) and sodium hydride (5.25 g) in THF (80 ml) was added dropwise. The orange reaction mixture was further refluxed for 65 h with continuous stirring and in a nitrogen atmosphere. The light-yellow reaction mixture obtained was filtered and the isolated sodium chloride washed with a small amount of hot THF. The tetrahydrofuran solution was concentrated, cooled, and then poured over crushed ice and macerated. The creamy viscous product obtained was left overnight. It was further macerated with crushed ice, 10% aqueous potassium hydroxide, and washed with water. Further maceration with methanol gave a solid which was dried in air. It was recrystallized from acetonitrile-methanol and dried in a vacuum oven at 90° C. to give 28 g of 20 as white crystalline solid, mp 104°–106° C.

EXAMPLE 9

Preparation of tris(4-aminophenoxy)tris(phenoxy)cyclotriphosphazene, 21

A 250-ml heater-equipped autoclave pressure bottle was charged with a solution of 20 (16.0 g) in aniline (40 ml), containing catalyst platinum oxide (0.075 g). The mixture was agitated vigorously at 50° C. and 60 psi of hydrogen until no further pressure drop was observed (3-4 h). The reaction mixture was filtered and concentrated under reduced pressure to 10 ml and poured slowly into hexane. The hexane was decanted off. The light brown paste was then extracted with hot hexane until the maceration was difficult. The thick paste was cooled in ice to give a light-yellow solid, which recrystallized from o-dichlorobenzene to give a white solid. The solid was further boiled with n-hexane, filtered, and dried to yield 21 (10.0 g). DTA examination of this solid showed a melting point range from 115°–145° C.

EXAMPLE 10

Preparation of tris-(4-maleamic acid phenoxy)tris-(phenoxy)cyclotriphosphazene, 22; also the bis-maleamic acid 23

To a magnetically stirred solution of 21 (5.535 g, 0.0075 mole) in N,N-dimethylacetamide (35.0 ml), granular maleic anhydride (2.242 g, 0.0228 mole) was added. The light-yellow solution was stirred overnight at ambient temperature under dry conditions. It was then poured over crushed ice. The yellow solid obtained was filtered, washed with water, and dried to yield the required maleamic acid 22 (6.0 g).

The bis-maleamic acid 23 was prepared by a similar method using two molar equivalents of maleic anhydride.

EXAMPLE 11

Preparation of tris-(4-maleimidophenoxy)trisphenoxy-cyclotriphosphazene, 24

A 25% solution of 23 in DMAC (8.0 ml) was heated in a shallow dish placed in a continuously circulated air oven maintained at 160°–162° C. for 0.5 h. At this stage the solvent was evaporated in readiness for polymerization. See Example 12 below.

EXAMPLE 12

Polymerization of Maleimide 24

Solvent was evaporated from the reaction mixture of Example 11 and the temperature of the oven was raised to 230°–232° C. and curing was performed for 1.5 hours.

The resulting brown polymer was further heated to 285°±2° C. for 0.25–0.5 hour to give the tough brown polymer 26.

By a similar procedure the bis-maleimide 25 may be polymerized to polymer 27.

Figure 3C:
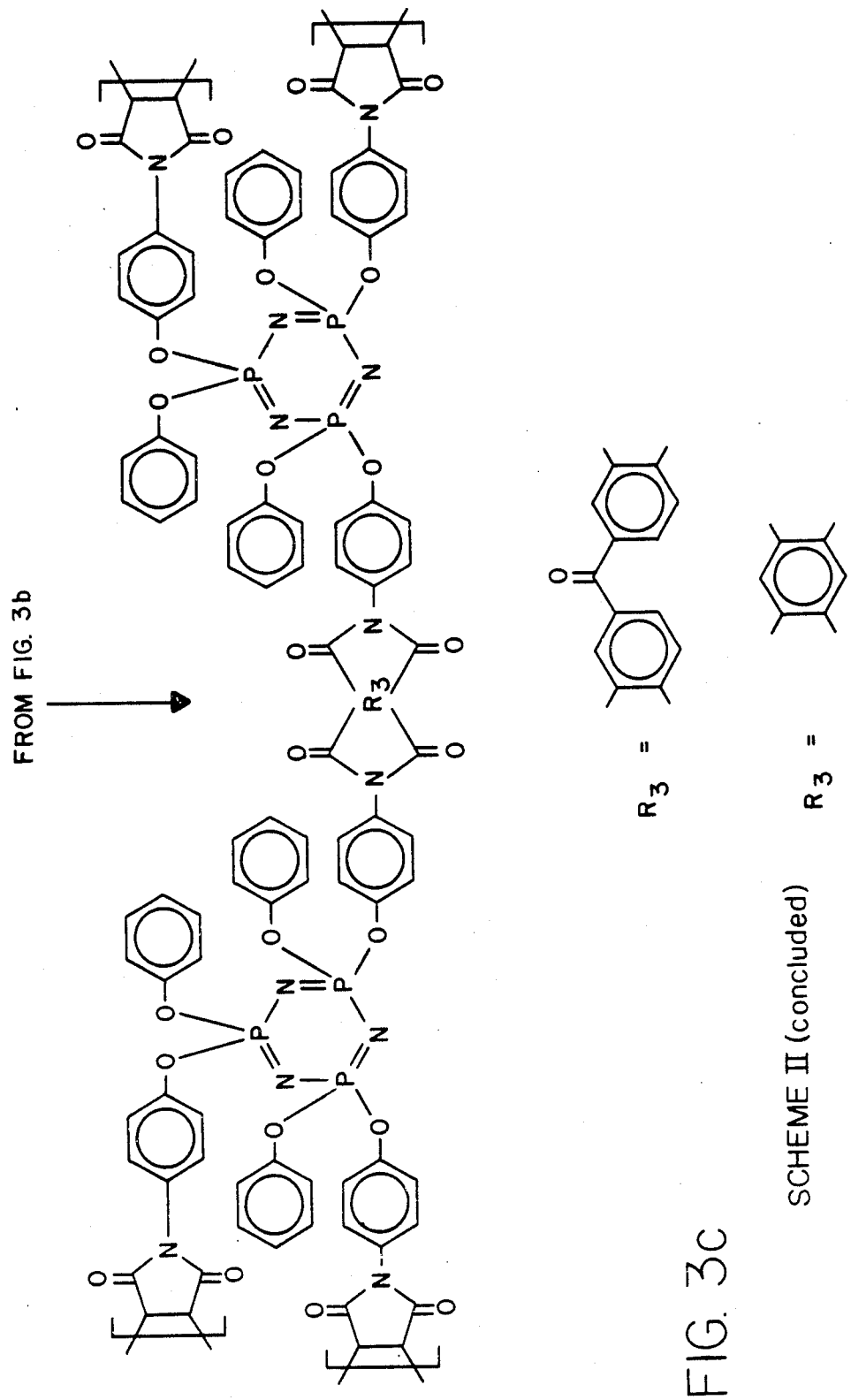
FIG. 3c shows the polymerization of the maleimides of FIG. 3b.

Referring to FIG. 3 (Scheme II) it will be seen that the tris amino compound 21 may be reacted with a dianhydride and with different proportions of maleic anhydride to afford different maleamic acids such as 28a, 28b and 28c which in turn may undergo ring closure to afford maleimides such as 29a, 29b and 29c, respectively. The following examples are illustrative.

EXAMPLE 13

The Tetrakismaleamic Acid 28a

This has the structure 28a shown in Scheme II where $R_3$ and $R_4$ are, respectively,

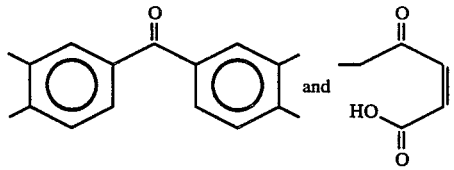

To a magnetically stirred solution of 21 (5.535 g, 0.0075 mole in DMAC (35.0 ml), granular maleic anhydride (1.5375 g, 0.01569 mole) was added. A dark yellow solution obtained just after addition changes to a light yellow color. To this solution, powdered benzophenonetetracarboxylic dianhydride (1.2083 g. 0.00375 mole) was added and stirring continued at ambient temperature for 8–10 hrs. The solution was then poured over crushed ice. The light-yellow solid obtained was filtered, washed with water, and dried to yield tetrakismaleamic acid 28a.

By using the appropriate molar proportions of maleic anhydride the maleamic acid 28b was prepared using a similar method. By using pyromellitic anhydride and the appropriate molar proportion of maleic anhydride the maleamic acid 28c was prepared using a similar method.

EXAMPLE 14

Imidization of Maleamic Acid 28c to Produce the Maleimide 29c

A solution of maleamic acid 28c in DMAC was heated in an air oven maintained at 160°–162° C. The reaction was monitored by IR with a sample on an NaCl disk heated concurrently. It was observed that the solvent evaporated within a few minutes of heating, leaving a light-yellow solid. An IR recording after the first few minutes of heating, showed a pattern indicating that complete cyclodehydration had taken place to give the imide 29c. Experience indicates that the solvent plays an important role at this stage.

By a similar method the maleamic acid 28a was converted to the maleimide 29a.

EXAMPLE 15

Polymerization of the Maleimides 29a, 29b and 29c

The maleimide, after removal of solvent, is heated typically at 160°–162° C. for 15–30 minutes, then at 232°–233° C. for 1.5 hours and then at 285°–300° C. for 15–30 minutes. Tough, dark polymers result having the repeating units shown in Scheme II.

Table III below shows proportions of reagents used in preparation of the various maleamic acids and Table IV shows thermal properties of the resulting polymers.

TABLE III

Proportions of Reagents Used in the Preparation of Maleamic Acids

| Maleamic acid | Trisamine 21 g | mole | Maleic anhydride g | mole | Aromatic dianhydride Type | g | mole |
|---|---|---|---|---|---|---|---|
| 22 | 5.535 | 0.0075 | 2.242 | 0.0228 | — | — | — |
| 23 | 5.535 | 0.0075 | 1.5375 | 0.01569 | — | — | — |
| 28a | 5.535 | 0.0075 | 1.5375 | 0.01569 | BPDA | 1.2083 | 0.00375 |
| 28b | 5.535 | 0.0075 | 0.7717 | 0.0078 | BPDA | 1.2083 | 0.00375 |
| 28c | 5.535 | 0.0075 | 1.5375 | 0.01569 | PMDA | 0.8175 | 0.00375 |

BPDA = benzophenonetetracarboxylic dianhydride
PMDA = pyromellitic dianhydride

TABLE IV

Thermal Properties of Polymers

| | In nitrogen | | | In air | | | |
|---|---|---|---|---|---|---|---|
| Polymer | PDT (°C.) | PDT$_{max}$ (°C.) (W*) | Char yield % @ 800° C. | PDT (°C.) | PDT$_{max}$ (°C.) (W*) | Char yield % @ 700° C., | 800° C. |
| 26 | 345 | — | 80 | 345 | 750 (68) | 77 | 48 |
| 27 | 345 | 410 (87) | 78 | 345 | 410 (93) 750 (60) | 73 | 42 |
| I | 350 | — | 79 | 350 | 770 (63) | 76 | 48 |
| II | 350 | — | 81 | 350 | 760 (68) | 78 | 49 |
| III | 350 | — | 82 | 350 | 770 (50) | 71 | 29 |

W* = weight remaining at the PDT$_{max}$ indicated.

In Table IV, polymers I, II and III have the structure shown in FIG. 3 and are derived from maleimides 29b, 29a and 29c, respectively.

The thermal stabilities of polymers 26, 27, I, II and III were investigated by using dynamic TGA. The polymer decomposition temperature (PDT), the temperatures at which the polymers maximum rate of weight loss occurred, (PDT$_{max}$), and the char yields, both in air and in nitrogen, are summarized in Table IV. The results show that the threshold temperature at which major thermal decomposition occurs is near 400° C. in nitrogen.

Interestingly, all these polymers have shown extremely high char yields both in nitrogen and air atmospheres, higher than most of the bismaleimides and other known polymers heretofore used for composite fabrication. These polymers showed char yields of 82–78% at 800° C. in nitrogen and 78–71% at 700° C. in air. The process of thermooxidative decomposition seems to be negligible up to 700° C., demonstrating that it would be possible to use these polymers in composites where thermo-oxidative stability as high as 700° C. in air atmosphere is required. However, above 700° C., a catastrophic decomposition in air is observed. These polymers are self-extinguishing and did not burn or melt when exposed to flame, indicating their virtually incombustible nature. Among the synthesized polymers, polymers I, II and III have improved thermal stability, which may be explained by the presence of aromatic imide as the linking group between two cyclotriphosphazene units. The high char yield is due to the presence of a unique combination of aromatic and heterocyclic groups, nitrogen, and phosphorus, and the absence of any aliphatic group in the synthesized polymers.

Figure 4B:
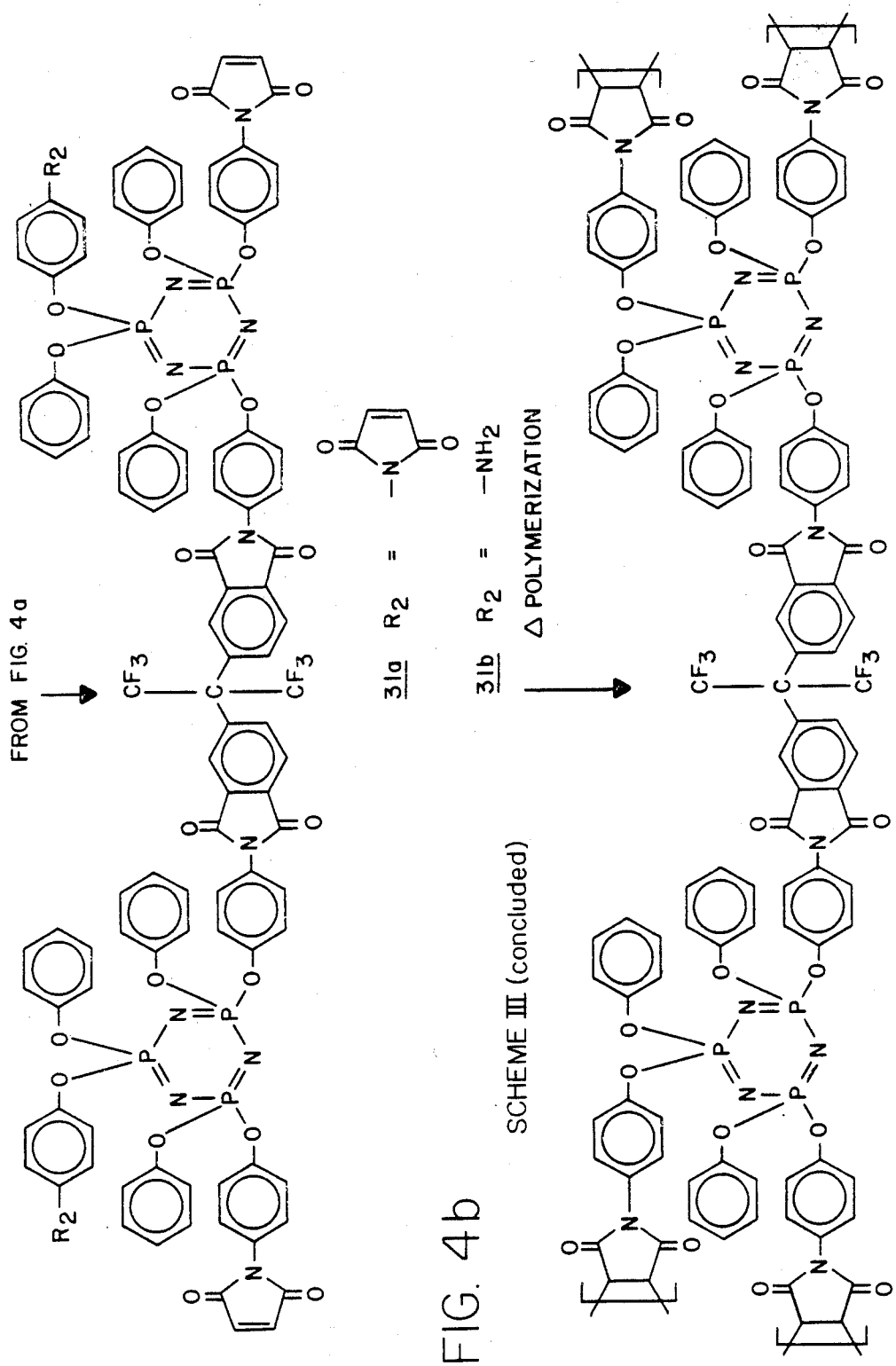
FIG. 4b shows the conversion of the maleamic acids of FIG. 4 to maleimides and their polymerization.

In Examples 16 to 19 the trisamino compound 21 was similarly reacted with maleic anhydride and 4,4'-hexafluoroisopropylidenediphthalic anhydride (HFDA) according to Scheme III which is shown in FIG. 4.

EXAMPLE 16

Reaction of Trisamino Compound 21 with Maleic Anhydride and HFDA to Produce Maleamic Acid 30

The tetrakis maleamic acid 30a, where R$_1$ =

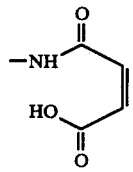

was prepared as follows:

To a magnetically stirred solution of 21 (5.535 g, 0.0075 mole) in DMAC (35.0 ml) at ambient temperature in presence of N$_2$, granular maleic anhydride (1.537 g. 0.01575 mole) was added. To the yellow solution, HFDA (1.665 g, 0.0037 mole) was added and the light-yellow solution was stirred for 1 h. It was poured over crushed ice, and the yellow solid obtained was filtered, washed with water, and dried to give the tetrakismaleamic acid 30a (7.5 g).

The bismaleamic acid 30b (R=H) was similarly obtained, using the 1:1:0.5 mole ratio of trisamine 21, maleic anhydride, and HFDA, respectively.

EXAMPLE 17

Imidazation of the Maleamic Acid 30a to the Imide 31a

A magnetically stirred DMAC solution of the tetrakismaleamic acid 30a in a nitrogen atmosphere was thermally cyclodehydrated in situ. The heating was performed in an oil bath maintained at 140°–145° C. for 1 h and then at 160°–165° C. for 1 h. After cooling, the light-brown solution was poured dropwise into continuously stirred cold methanol. The light-yellow solid obtained was macerated with fresh methanol, filtered, and dried to give the desired maleimide 31a (5.8 g).

Tetrakismaleimide 31a was also obtained with the solution of tetrakismaleamic acid 30a heated at 160°–162° C. for 10–20 min in a shallow dish placed in a circulating-air oven.

The bis-maleimide 31b (R=NH$_2$) was obtained similarly from the bis-maleamic acid 30b.

EXAMPLE 18

Polymerization of the Maleimide 31a

The yellow powder of tetrakismaleimide 31a was heated at 165°–170° C. in an air oven; it was seen to melt in this temperature range, which was maintained for 0.5 h. The brown polymer 32a was obtained on curing at 235°-240° C. for 1.5 h and further at 285±5° C. for 10-15 min.

Polymer 32a was also obtained when the solution of tetrakismaleamic acid 30a was heated in a shallow aluminum dish placed in a continuously circulating air oven. Curing was performed under similar conditions.

Polymer 32b was similarly obtained from maleimide 31b prepared from maleamic acid 30b.

The thermal behaviors of thermosets 32a and 32b were investigated by dynamic thermogravimetric analysis in both air and nitrogen atmospheres. The polymer decomposition temperature (PDT), the temperature at which the polymers' maximum rate of weight loss occurred (PDT$_{max}$), and the char yields, both in air and nitrogen, are summarized in Table V. The results show that the polymers were stable up to 375°-380° C. in both air and nitrogen atmosphere, with the maximum thermo-oxidative decomposition taking place mainly beyond 700° C. in air. These thermo-setting polymers show high char yields. Polymer 32a showed a char yield of 80% at 800° C. in nitrogen, and of 68% at 700° C. in air.

Isothermal TGAs of polymer 32a were done in nitrogen at 350° C., 450° C., 550° C., and 650° C., and in air at 260° C., 350° C., 450° C., and 550° C., respectively, and are shown in Table VI. In air at 260° C. after 72 h a weight loss of 1.8% was observed. A weight loss of 1.2% was seen in nitrogen at 350° C. after 24 h; in air, it was 7.5%. Although a degradation mechanism based on these data has not been deduced, it may be said that the initial losses at temperatures above 350° C., both in air and nitrogen, may be caused by the presence of phenoxy groups.

EXAMPLE 19

Composite Fabrication

Test laminates were prepared by coating graphite cloth (eight-harness satin weave cloth, designed as style 133 fabric), with a methyl ethyl ketone or dimethylacetamide solution (50%) of tetrakismaleimide 31a and drying the prepregs in an air oven at 105°-110° C. for 5-10 min. The prepregs (eight or four plies) were stacked in a vacuum-bag and pressed between aluminum plates in a heated press maintained at 169°-170° C. for 30 min, 235°-240° C. for 1.5 h, and 285°-290° C. for 15 min. The pressure during curing was maintained at 50-70 psi. A slow cooling was preferred, holding for 10 min at 230°-240° C. and then for 30 min at 160° C. Laminates from 31a can also be obtained by hot-melting. The results of the evaluation of mechanical properties are given in Table VII.

The resin contents of the laminates were determined by boiling with hydrazine for 2 h. Moisture absorptions were determined by boiling in water. The limiting oxygen index tests (LOI) performed both at room temperature and at 300° C., showed a 100% LOI value, indicating their virtual incombustible nature. Dynamic mechanical analysis (DMA) determinations were performed on four-ply laminates; the glass-transition temperature (Tg) was found to be 322° C.

The density and the shear, tensile, and flexural strengths of an eight-ply laminate were determined; the values are compared with the commonly used bismaleimide and epoxy resins in Table VII. An improved elastic tensile modulus, tensile strength, energy under stress/strain curve, flexural strength, and modulus can be attributed to the presence of phenoxy and hexafluoroisopropylidene groups.

Tables V, VI and VII illustrate thermal properties of polymers 32a and 32b and mechanical properties of laminates.

TABLE V

Thermal Properties of Polymers 32a and 32b

| Polymer | In nitrogen | | | In Air | | | |
|---|---|---|---|---|---|---|---|
| | PDT, °C. | PDT$_{max}$, °C. (W*)$^a$ | Char yield, % 800° C. | PDT, °C. | PDT$_{max}$, °C. (W*)$^a$ | Char yield, % 700° C. | Char yield, % 800° C. |
| 32a | 380 | — | 80 | 375 | 540 (84) 750 (60) | 68 | 48 |
| 32b | 375 | 490 (90) | 78 | 375 | 530 (85) 750 (44) | 60 | 27 |

$^a$W* = weight remaining at that temperature

TABLE VI

Isothermal TGA

| Polymer | In nitrogen | | | In air | | |
|---|---|---|---|---|---|---|
| | Temp, °C. | Time, h | Loss of weight | Temp, °C. | Time, h | Loss of weight |
| 32a | — | — | — | 260 | 72 | 1.8 |
| | 350 | 24 | 1.2 | 350 | 24 | 7.5 |
| | | | | | 72 | 12.0 |
| | 450 | 24 | 19.0 | 450 | 12 | 60.0 |
| | 550 | 24 | 50.0 | 550 | 1 | 30.0 |
| | | | | | 12 | 92.0 |
| | 650 | 24 | 80.0 | — | — | — |

TABLE VII

Mechanical Properties of Graphite-Cloth Laminates from Resin 31a

| Property tested | Test method | Value | | |
|---|---|---|---|---|
| | | Resin 31a | Bismaleimide$^a$ | Epoxy$^b$ |
| Resin content, % | Hydrazine method | 22.5 | 34.3 | 25 |
| Density, g/cm$^3$ | | 1.47 | 1.554 | 1.57 |
| LOI, %, O$_2$ | | | | |
| Room temperature | ASTM D 2863 | 100.0 | 58.4 | 45.0 |
| 300° C. | ASTM D 2863 | 100.0 | | |
| Flexural strength | | | | |
| psi | ASTM D 790 | 71,086 | 40,014 | 79,808 |
| MN/m$^2$ | ASTM D 790 | 490.5 | 276 | 550 |
| Flexural modulus | | | | |
| psi | ASTM D 790 | 8.2 × 10$^6$ | 7.03 × 10$^6$ | 6.8 × 10$^6$ |

TABLE VII-continued
Mechanical Properties of Graphite-Cloth Laminates from Resin 31a

| Property tested | Test method | Value Resin 31a | Bismaleimide[a] | Epoxy[b] |
|---|---|---|---|---|
| MN/m$^2$ | ASTM D 790 | 56,673 | 48,461 | 46,880 |
| Energy under stress/strain curve | | | | |
| ft/lb | ASTM D 790 | 18.5 | — | — |
| Short beam shear | | | | |
| psi | ASTM D 2344 | 4,250 | 3,567 | 7,749 |
| MN/m$^2$ | ASTM D 2344 | 29.3 | 24.59 | 53.42 |
| Tensile strength | | | | |
| psi | ASTM D 638 | 59,213 | 21,286 | 51,639 |
| MN/m$^2$ | ASTM D 638 | 408.5 | 147 | 356 |
| Elastic tensile modulus | | | | |
| psi | ASTM D 638 | 5.45 × 10$^6$ | 2.5 × 10$^6$ | 4.4 × 10$^6$ |
| MN/m$^2$ | ASTM D 638 | 37,605 | 17,235 | 30,330 |
| Water absorption[c] | | | — | — |
| 2 h boiling | | | 1.91 | |
| 24 h boiling | | | 2.42 | |

[a]Bismaleimide of 4,4'-diaminodiphenylmethane.
[b]Epoxy Ciba-Geigy MY-720 (tetraglycidylamine of 4,4'-diaminodiphenylmethane cured with 4,4'-diaminodiphenylsulfone (DDS)).
[c]Laminate pieces of 0.75 × 0.5 × 0.009 inches tested.

An Alternative and Preferred Method of Synthesizing 4-Aminophenoxycyclotriphosphazenes The method described above, e.g. in Examples 1 and 2, forms a 4-nitrophenoxycyclotriphosphazene and reduces the nitro group to amino groups. This requires high pressures and high pressure equipment. An advantageous, preferred method is as follows and is applicable to anilino compounds (X=NH) as well

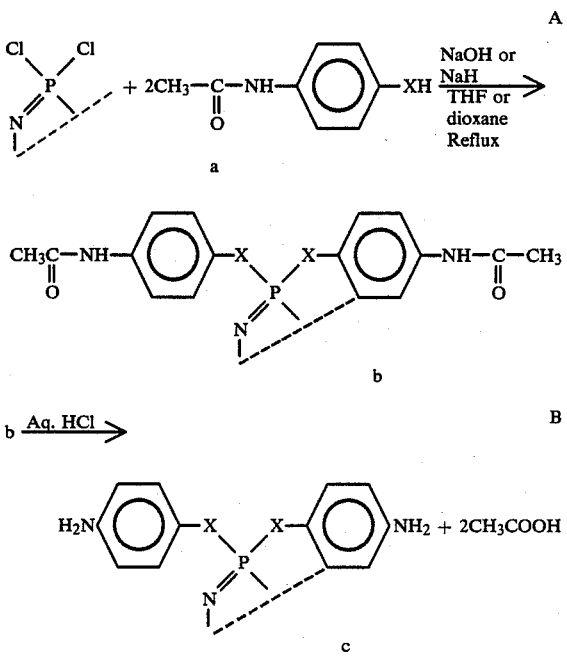

Other amides or imides may be used as a instead of the acetamide shown. If pyridine is used in reaction A it will function both as a solvent and acid acceptor, hence an acid acceptor such as NaOH or NaH is unncessary. In these reactions, X=O or NH.

This method avoids the need to form nitro intermediates. Both reactions A and B are facile reactions which proceed at moderate temperatures and atmospheric pressure.

The use of Anilino Analogues

As stated above, the anilino analogues,

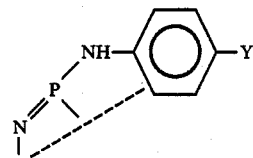

(Y=H or NH$_2$) may be prepared and used instead of phenoxy compounds. The production of such anilino precursors, intermediates (maleamic acids, maleimides) and polymers is analogous and the polymers exhibit similr fire and heat resistant properties.

We claim:
1. A cyclotriphosphazene having the structure:

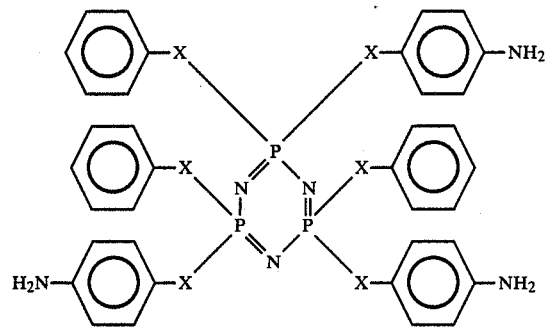

wherein X is oxygen (—O—) or secondary amino (—NH—).

2. The cyclotriphosphazene of claim 1 wherein X is oxygen.

3. The cyclotriphosphazene of claim 1 wherein X is secondary amino (—NH—).

* * * * *